US012460344B2

(12) United States Patent
Charpenay

(10) Patent No.: US 12,460,344 B2
(45) Date of Patent: Nov. 4, 2025

(54) AUTOMATIC IRONING APPARATUS

(71) Applicant: Einsen Innovations PTY LTD, Perth (AU)

(72) Inventor: Josselin Meng Norbert Charpenay, Perth (AU)

(73) Assignee: Einsen Innovations PTY LTD, Perth (AU)

( * ) Notice: Subject to any disclaimer, the term of this patent is extended or adjusted under 35 U.S.C. 154(b) by 243 days.

(21) Appl. No.: 17/999,139

(22) PCT Filed: Jun. 3, 2021

(86) PCT No.: PCT/AU2021/050552

§ 371 (c)(1),
(2) Date: Nov. 17, 2022

(87) PCT Pub. No.: WO2021/243413

PCT Pub. Date: Dec. 9, 2021

(65) Prior Publication Data

US 2023/0349091 A1 Nov. 2, 2023

(30) Foreign Application Priority Data

Jun. 3, 2020 (AU) ................................ 2020901827

(51) Int. Cl.
*D06F 63/00* (2006.01)
*A61L 2/10* (2006.01)
(Continued)

(52) U.S. Cl.
CPC ................ *D06F 63/00* (2013.01); *A61L 2/10* (2013.01); *D06F 67/02* (2013.01); *D06F 67/04* (2013.01);
(Continued)

(58) Field of Classification Search
CPC ........ D06F 87/00; D06F 89/02; D06F 89/023; D06F 89/00; D06F 63/00; D06F 67/02; D06F 67/04
See application file for complete search history.

(56) References Cited

U.S. PATENT DOCUMENTS 1,981,954 A 11/1934 Heller, Sr.
4,980,981 A * 1/1991 Naidoo .................. D06F 69/00 38/144
(Continued)

FOREIGN PATENT DOCUMENTS

CN 109281143 A 1/2016
CN 206736596 U 12/2017
(Continued)

OTHER PUBLICATIONS

International Search Report for International Application No. PCT/AU2021/050552, mailed Aug. 31, 2021, 5 pages.
International Written Opinion for International Application No. PCT/AU2021/050552, mailed Aug. 31, 2021, 8 pages.

*Primary Examiner* — Nathan E Durham
(74) *Attorney, Agent, or Firm* — TraskBritt

(57) ABSTRACT

Provided is automatic ironing apparatus comprising a housing defining a passage therethrough, a guiding arrangement configured to guide an article of clothing through the passage, and a pre-treatment assembly within the housing and configured to pre-treat the article of clothing as the article is guided through the passage. Also included is a primary treatment assembly within the housing and configured to treat the article of clothing as the article is guided through the passage, as well as a post-treatment assembly configured to post-treat the article of clothing as the article is guided through the passage. Apparatus also includes a controller configured to control the guiding arrangement and treatment assemblies, as well as energizing means configured to provide electrical energy to the controller, guiding arrangement
(Continued)

and treatment assemblies, wherein each treatment facilitates ironing of the article of clothing as the article is guided through the passage.

12 Claims, 5 Drawing Sheets

(51) Int. Cl.

| | |
|---|---|
| ***D06F 67/02*** | (2006.01) |
| ***D06F 67/04*** | (2006.01) |
| ***D06F 87/00*** | (2006.01) |
| ***D06F 89/02*** | (2006.01) |

(52) U.S. Cl.

CPC .............. *D06F 87/00* (2013.01); *D06F 89/02* (2013.01); *D06F 89/023* (2013.01); *A61L 2202/11* (2013.01); *A61L 2202/26* (2013.01)

(56) References Cited

U.S. PATENT DOCUMENTS

| | | | |
|---|---|---|---|
| 8,443,531 B2 | 5/2013 | Lapauw et al. | |
| 2010/0212866 A1 | 8/2010 | Bringewatt et al. | |
| 2017/0159232 A1* | 6/2017 | Kitagawa ................ | D06F 89/02 |
| 2019/0309465 A1* | 10/2019 | Rozov ................ | A41H 43/0257 |

FOREIGN PATENT DOCUMENTS

| | | | |
|---|---|---|---|
| CN | 106120274 | B | 3/2018 |
| CN | 209498667 | U | 10/2019 |
| EP | 1403417 | A1 | 3/2004 |
| EP | 1602775 | B1 | 9/2007 |
| EP | 2998434 | A1 | 3/2016 |
| GB | 0667178 | A | 2/1952 |
| JP | 6349200 | A | 3/1988 |
| WO | 2019/038752 | A1 | 2/2019 |

* cited by examiner

AUTOMATIC IRONING APPARATUS

CROSS-REFERENCE TO RELATED APPLICATIONS

This application is a national phase entry under 35 U.S.C. § 371 of International Patent Application PCT/AU2021/050552, filed Jun. 3, 2021, designating the United States of America and published as International Patent Publication WO 2021/243413 A1 on Dec. 9, 2021, which claims the benefit under Article 8 of the Patent Cooperation Treaty to Australian Patent Application Serial No. 2020901827, filed Jun. 3, 2020.

TECHNICAL FIELD

This disclosure relates to the field of ironing in general and, more specifically, to an automatic ironing apparatus and an associated method of automatic ironing.

BACKGROUND

The following discussion of the background art is intended to facilitate an understanding of the present disclosure only. The discussion is not an acknowledgement or admission that any of the material referred to is or was part of the common general knowledge as at the priority date of the application.

As is generally known in the art, ironing is the act of smoothing or pressing, typically with a heated iron, clothes, linens or similar fabrics or materials in order to remove wrinkles. As such, ironing typically involves the use of a small appliance, usually a heated tool (such as an iron), to remove wrinkles from fabric. A temperature of the heated iron typically depends on the material or fabric to be ironed, with common temperature around 180-220° Celsius (356-428 Fahrenheit).

Ironing generally works by loosening the bonds between the long-chain polymer molecules in the fibers of the material. While the molecules are hot, the fibers are straightened by the weight of the iron, and they hold their new shape as they cool. Some fabrics, such as cotton, require the addition of water to loosen the inter-molecular bonds. Similarly, other chemicals may be used to facilitate the ironing process.

While ironed clothes typically provide a neat, professional and well-groomed appearance to a wearer, the task of ironing is generally arduous and time-consuming. As a result, many people spend considerable time every day ironing clothes for work and social gatherings where a neat and professional appearance is desired.

The current disclosure was conceived with the goal in mind of automating ironing, or at least ameliorating conventional ironing practices.

BRIEF SUMMARY

The skilled addressee is to appreciate that reference herein to the term "treat" or "treatment" generally refers to the act or instance of subjecting something, such as an article of clothing, material or fabric, to some agent or action in order to bring about a particular result. In addition, reference to an article of clothing also includes reference to a portion of fabric or material that may not necessarily be configured for raiment, such as a napkin or serviette, a handkerchief, or the like.

According to a first aspect of the disclosure, there is provided automatic ironing apparatus comprising:

a housing defining a passage therethrough;

a guiding arrangement configured to guide an article of clothing through the passage;

at least one treatment assembly within the housing and configured to treat the article of clothing as the article is guided through the passage;

a controller configured to control the guiding arrangement and treatment assemblies; and energizing means configured to provide electrical energy to the controller, guiding arrangement and treatment assemblies, wherein each treatment facilitates ironing of the article of clothing as the article is guided through the passage.

Typically, the housing is shaped and dimensioned to be man-portable.

In an embodiment, the housing defines an inlet on one side and an outlet on an opposite side thereof, the inlet and outlet arranged in register via the passage.

In an embodiment, the guiding arrangement comprises a folding assembly configured to fold an article of clothing.

In an embodiment, the folding assembly comprises at least two articulated plates slidably arranged within the housing, the plates configured to interact to urge an article of clothing placed thereon into a predetermined orientation.

In an embodiment, the folding assembly includes at least one manipulation member configured to interact with the articulated plates in order to interact to urge an article of clothing placed thereon into a predetermined orientation.

In an embodiment, the folding assembly defines at least one channel configured to facilitate passage of a portion of an article of clothing through the passage when urged into a predetermined orientation.

Typically, the guiding arrangement includes at least one sensor configured to sense a presence of the article of clothing at the inlet of the housing, the sensed presence communicated to the controller to control the guiding arrangement accordingly.

In an embodiment, the sensor is configured to sense characteristics of the article of clothing, such as fabric type, fabric composition, fabric density, or the like.

In an embodiment, the guiding arrangement includes at least one roller configured to feed the article of clothing through the passage.

In an embodiment, the guiding arrangement includes an endless belt conveyor feeder configured to feed the article of clothing through the passage.

In an embodiment, the guiding arrangement includes a hanger urger mechanism configured to engage a suitable hanger in receipt of such article of clothing and to urge the hanger through the passage.

In an embodiment, the at least one treatment assembly comprises a pre-treatment assembly within the housing and configured to pre-treat the article of clothing as the article is guided through the passage.

In an embodiment, the at least one treatment assembly comprises a primary treatment assembly within the housing and configured to primary treat the article of clothing as the article is guided through the passage.

In an embodiment, the at least one treatment assembly comprises a post-treatment assembly configured to post-treat the article of clothing as the article is guided through the passage.

Typically, the pre-treatment assembly includes a fluid applicator configured to pre-treat the article of clothing by applying an ironing fluid thereto.

In an embodiment, the fluid applicator includes atomizer nozzles for spraying the ironing fluid onto the article of clothing.

Typically, the primary treatment assembly comprises at least one plate and/or roller configured to iron the article of clothing as the article passes through the passage, e.g., applying heat and/or pressure thereto.

In an embodiment, the primary treatment plate(s) and/or roller(s) is heated to facilitate primary treatment ironing.

In an embodiment, the primary treatment plate(s) and/or roller(s) comprises fluid channels and/or nozzles for delivering ironing fluid to the plate(s) and/or roller(s) during primary treatment of the article of clothing.

In an embodiment, the fluid channels deliver water that is converted to steam on a surface of the plate(s) and/or roller(s) during primary treatment.

In an embodiment, the primary treatment assembly includes a steam chamber through which the article of clothing is passed in order to facilitate primary treatment ironing.

Typically, the post-treatment assembly comprises a fluid applicator configured to post-treat the article of clothing by applying a post-treatment fluid thereto.

Typically, the fluid applicator includes a steam applicator for applying high temperature steam to the article of clothing for hygienic purposes.

In an embodiment, the fluid applicator includes a scent applicator configured to apply a particular scent or pleasant odor to the article of clothing.

In an embodiment, the post-treatment assembly comprises an infra-red (IR) emitter configured to post-treat the article of clothing by applying infra-red or near infra-red radiation thereto in order to facilitate evaporation of ironing fluid therefrom.

In an embodiment, the post-treatment assembly comprises an ultra-violet emitter configured to post-treat the article of clothing by applying ultra-violet radiation thereto in order to facilitate elimination of bacteria therefrom.

In an embodiment, the post-treatment assembly comprises an ultrasonic emitter configured to post-treat the article of clothing by applying ultrasonic radiation thereto in order to facilitate evaporation of ironing fluid therefrom.

In an embodiment, the post-treatment assembly comprises an electrostatic discharge emitter configured to post-treat the article of clothing by applying electrostatic discharge thereto in order to facilitate loosening of intermolecular bonds of the fabric of the article of clothing.

In an embodiment, the post-treatment assembly comprises a thermoelectric heat recovery mechanism configured to recover heat energy from the article of clothing.

In an embodiment, such recovered heat energy is provided to the electrostatic discharge emitter.

In an embodiment, the post-treatment assembly comprises at least one pressure roller configured to post-treat the article of clothing by applying a predetermined amount of pressure thereto in order to facilitate wrinkle removal.

In an embodiment, the at least one pressure roller comprises an outer layer of material, such as thermal foam, sponge, or fabric to impede mechanical damage to fasteners of the article of clothing, e.g., buttons, clasp locker, etc.

Typically, the controller is configured to control the guiding arrangement and treatment assemblies according to a sensed characteristic of the article of clothing.

In an embodiment, the controller is programmed with a specific treatment regime for an article of clothing, the treatment regime determined by the sensed characteristics.

In an embodiment, the controller is programmed with a specific treatment regime for an article of clothing, the treatment regime manually selectable by a user.

Accordingly, in such an embodiment, the controller typically includes a suitable user interface to allow treatment regime selection.

Typically, the energizing means comprises an electrical power supply operatively drawing power from a mains power connection and/or suitable electrochemical cells, such as batteries.

According to a second aspect of the disclosure, there is provided a method of automatic ironing that comprises the steps of:

- providing automatic ironing apparatus in accordance with the first aspect of the disclosure; and
- inserting an article of clothing into a passage of the apparatus so that the apparatus automatically irons the article of clothing.

In an embodiment, the method may include the step of a user selecting a suitable treatment regime for the apparatus to treat the article of clothing.

According to further aspects of the present disclosure, there is provided an automatic ironing apparatus substantially as herein described and/or illustrated.

BRIEF DESCRIPTION OF THE DRAWINGS

The description will be made with reference to the accompanying drawings in which.

DETAILED DESCRIPTION

Figure 1:
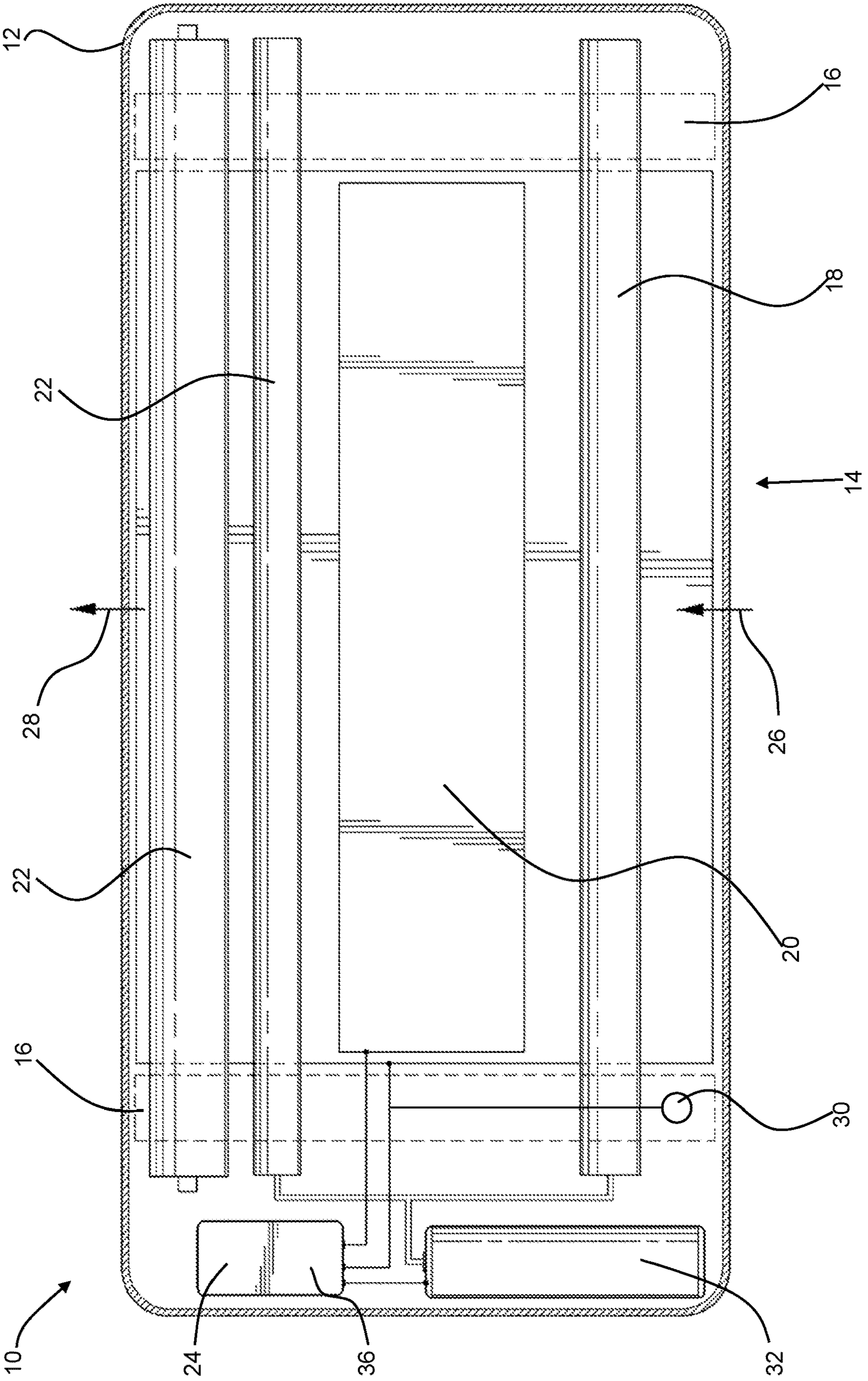
FIG. 1 is a diagrammatic top-view representation of one embodiment of automatic ironing apparatus, in accordance with an aspect of the present disclosure.
Figure 2:
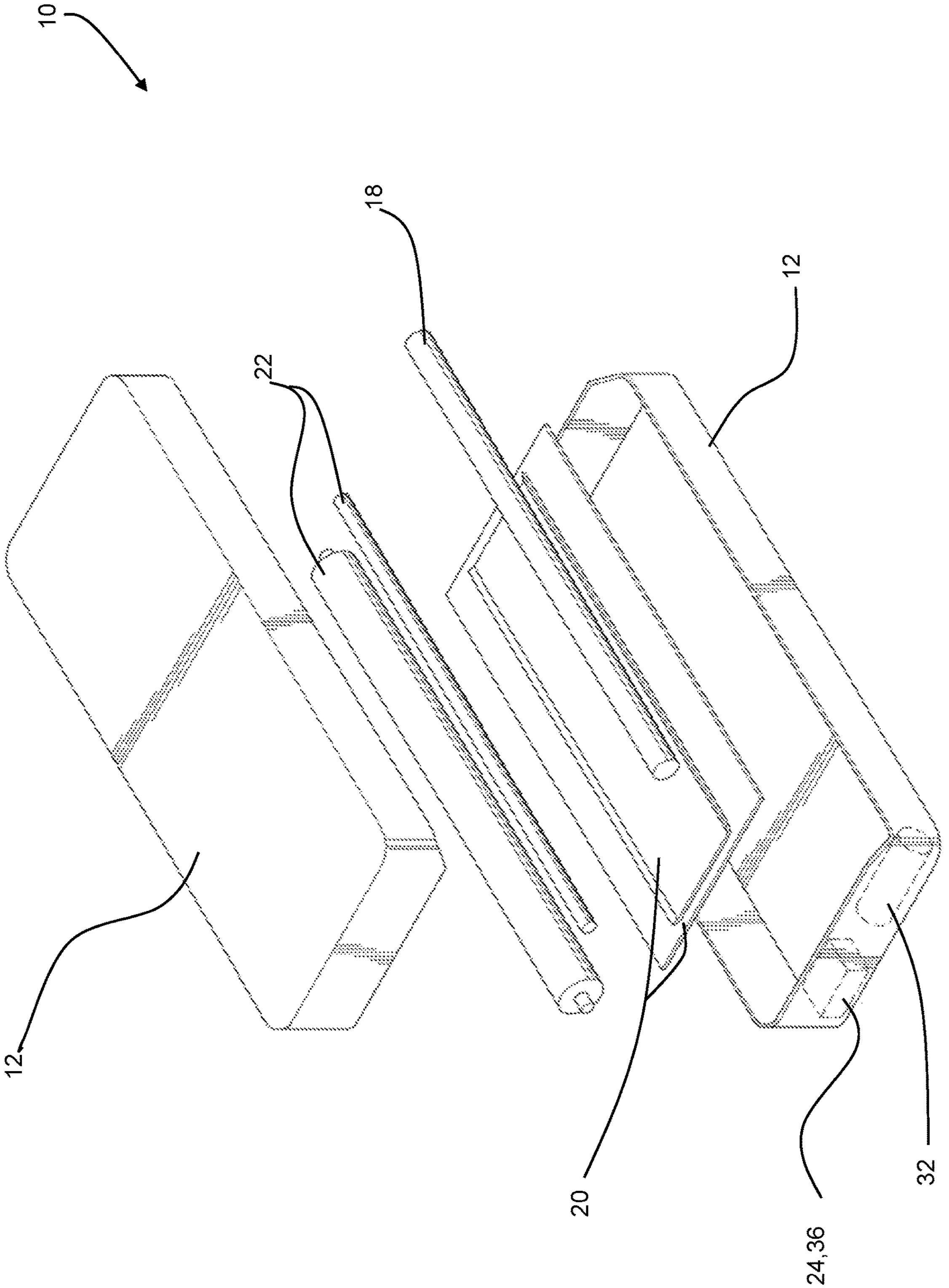
FIG. 2 is a diagrammatic exploded perspective-view representation of the automatic ironing apparatus of FIG. 1.
Figure 3:
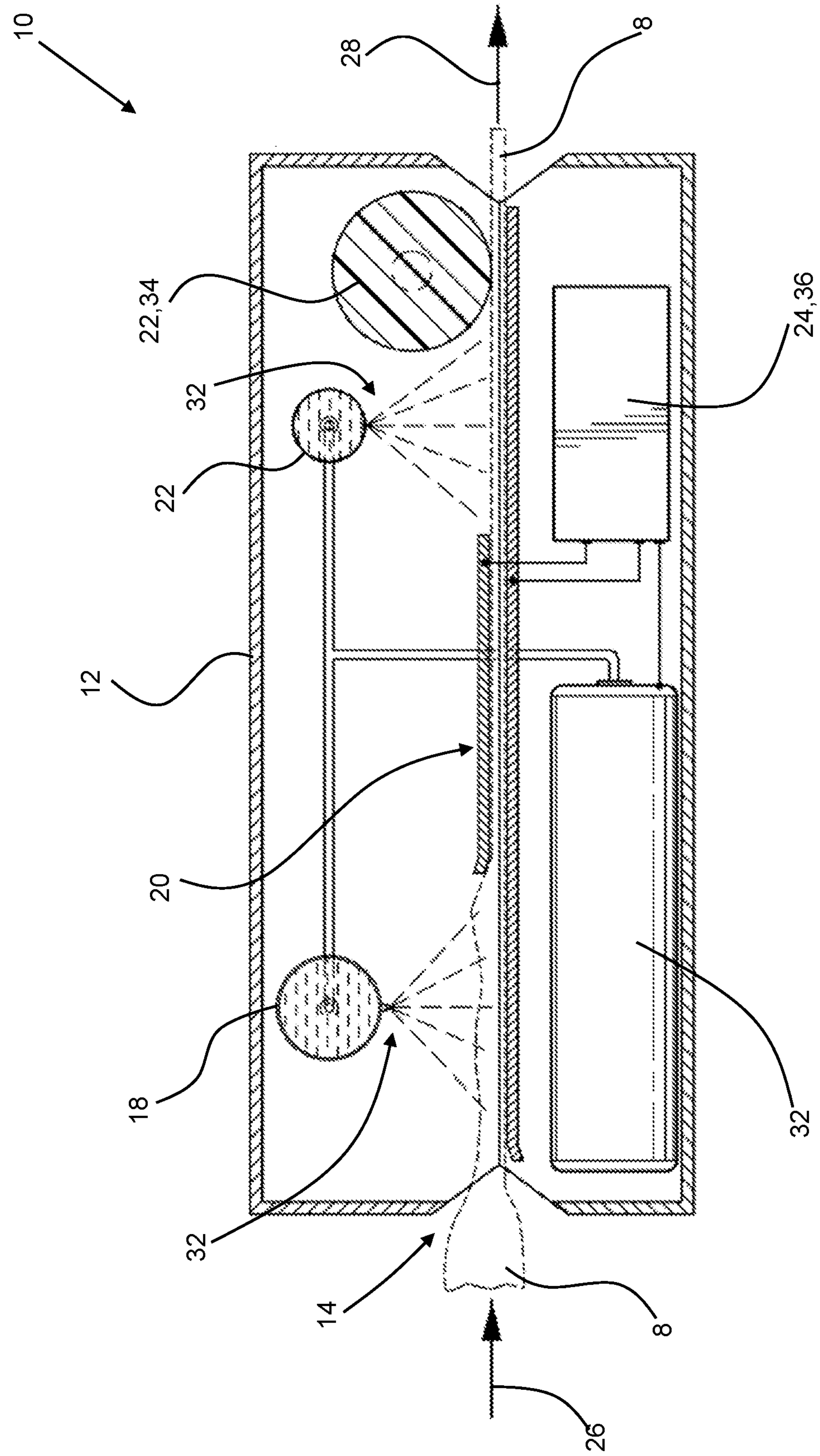
FIG. 3 is diagrammatic side-sectional view representation of the automatic ironing apparatus of FIG. 1.

Further features of the present disclosure are more fully described in the following description of several non-limiting embodiments thereof. This description is included solely for the purposes of exemplifying the present disclosure to the skilled addressee. It should not be understood as a restriction on the broad summary, disclosure or description of the disclosure as set out above.

In FIGS. 1 through 6, incorporated to illustrate features of the example embodiment or embodiments, like reference numerals are used to identify like parts throughout. The skilled addressee is to appreciate that the embodiment exemplified in the accompanying figures is but one possible example and that different embodiments may feature different aspects as generally herein described but not necessarily shown in the figures.

With reference now to FIGS. 1 through 6, there is shown one possible example of automatic ironing apparatus 10, which broadly comprises a housing 12, guiding arrangement 16, treatment assemblies 18, 20 and 22, a controller 24, as well as suitable energizing means 36. Apparatus 10 is intended to find particular application in automatic ironing of the article of clothing 8, wherein each treatment applied by the respective treatment assemblies 18, 20 and 22 facilitates ironing of the article of clothing 8 as the article is guided through passage 14 through the housing 12.

Apparatus 10 generally comprises a housing 12 that houses the constituent parts and typically defines a passage 14 therethrough. The housing 12 is typically shaped and dimensioned to be man-portable and may represent the appearance of a desktop printer in some embodiments. In the example shown, the housing 12 defines an inlet 26 on one side and an outlet 28 on an opposite side thereof, with the inlet 26 and outlet 28 arranged in register with each other via the passage 14.

It is to be appreciated that the housing 12 may be manufactured from a polymer material in one embodiment, such as a specific composite, that provides a strong yet lightweight housing for the constituent parts of apparatus 10. While passage 14 is shown passing substantially transversely through housing 12, variations hereon are possible and within the scope of the present disclosure.

Apparatus 10 also generally includes guiding arrangement 16, which is configured to guide the article of clothing 8 through the passage 14. Importantly, the guiding arrangement 16 may include a sensor 30 that is configured to sense a presence of the article of clothing at the inlet 26 of the housing 12. This sensed presence is generally communicated to the controller 24 in order to control the guiding arrangement 16 and treatment assemblies 18, 20, 22 (described below) accordingly.

Figure 4:
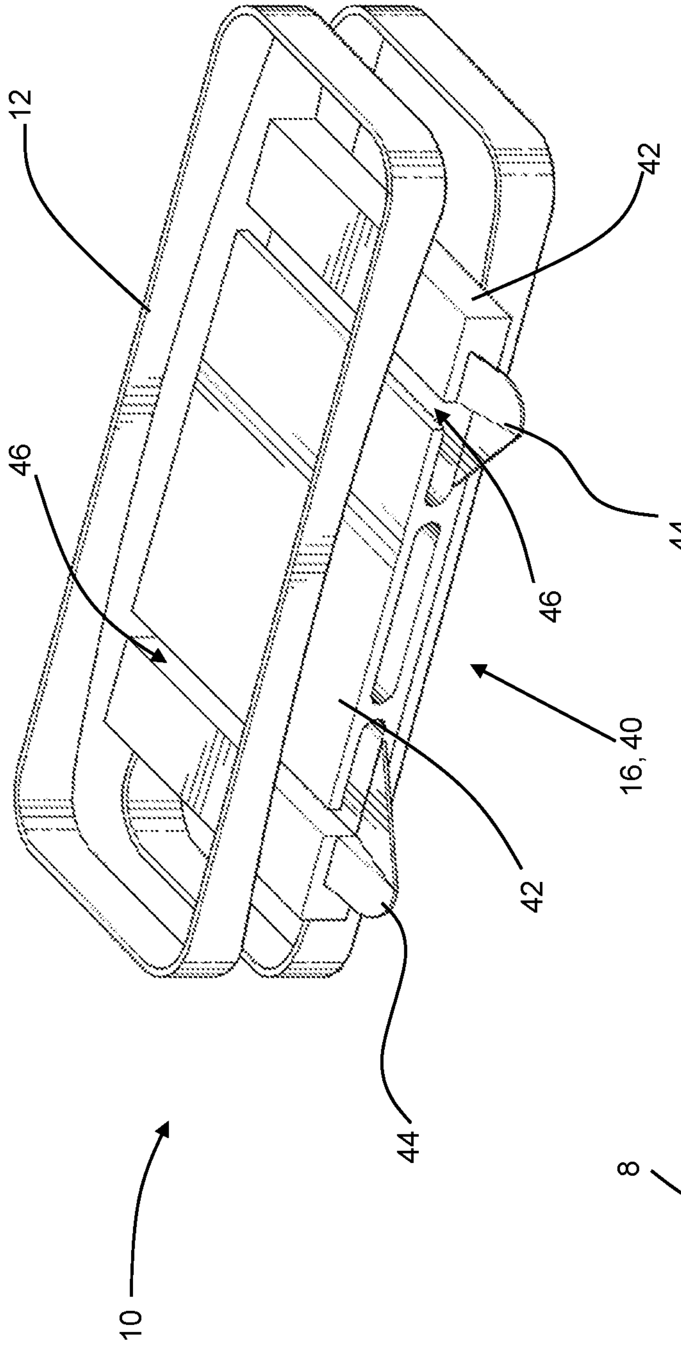
FIG. 4 is a diagrammatic perspective-view representation of one embodiment of the automatic ironing apparatus showing a folding assembly thereof, in accordance with aspects of the present disclosure.
Figure 5:
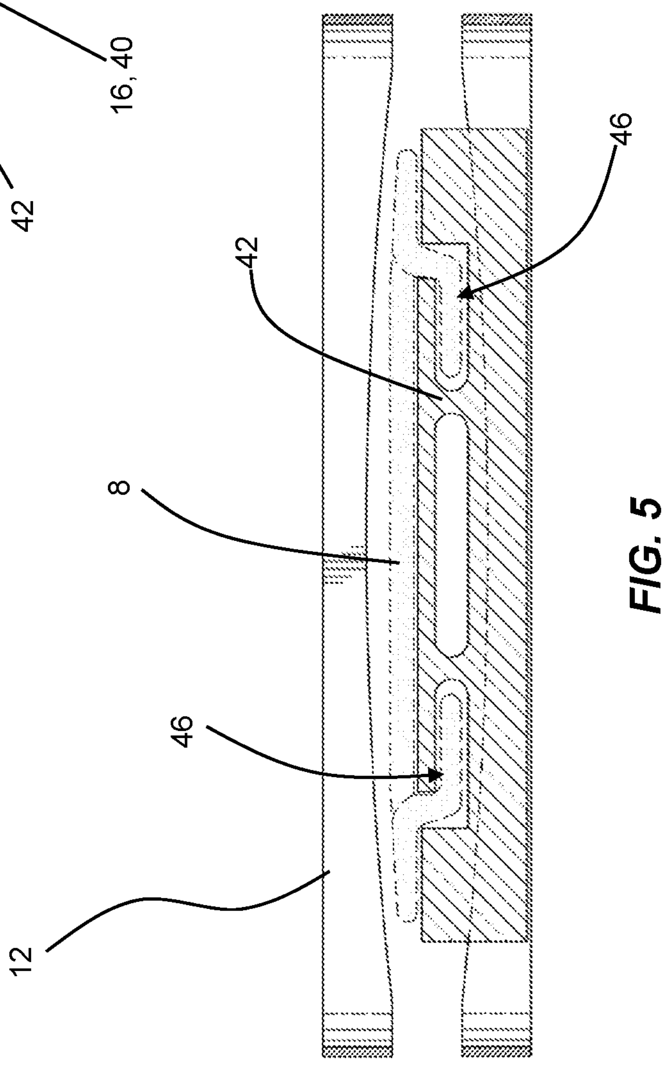
FIG. 5 is a diagrammatic side-view representation of the automatic ironing apparatus of FIG. 4.
Figure 6:
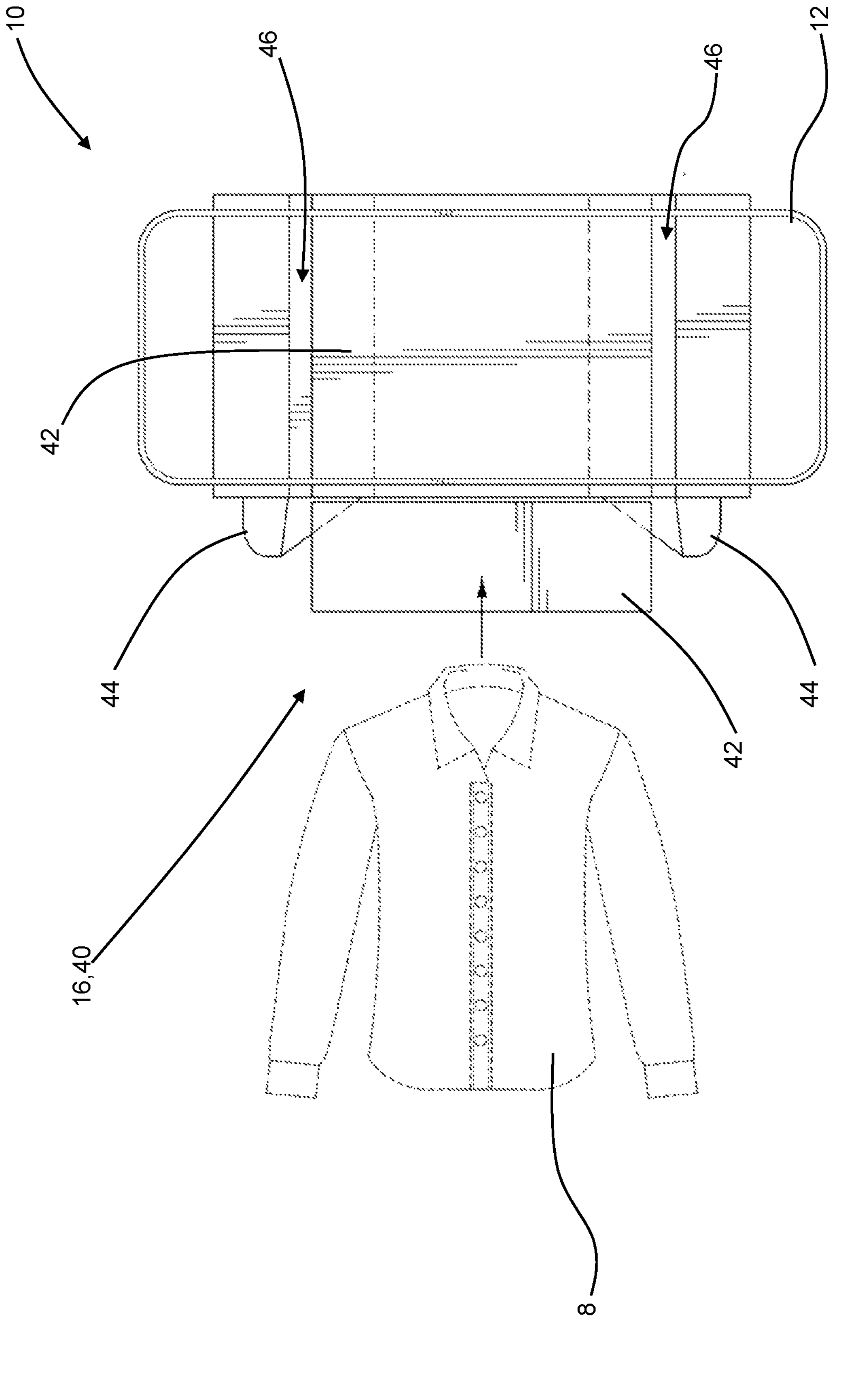
FIG. 6 is diagrammatic top-view representation of the automatic ironing apparatus of FIG. 4.

In one embodiment, examples of which are shown in FIGS. 4 through 6, the guiding arrangement 16 comprises a folding assembly 40 that is configured to fold an article of clothing 8. Such folding may be done prior, during or after the article of clothing passing through the passage 14, requirements depending. For example, a business shirt may be folded to facilitate ironing as it is guided into the housing 12 prior to reaching the pre-treatment assembly 18, as it exits apparatus 10 after ironing, and/or the like.

In an embodiment, the folding assembly 40 comprises at least two articulated plates 42 that are slidably arranged within the housing and/or relative to each other. These plates 42 are typically configured to interact to urge an article of clothing 8 placed thereon into a predetermined orientation before, during or after passing through the passage 14. In an embodiment, the folding assembly 40 includes at least one manipulation member 44 that is configured to interact with the articulated plates 42 in order to interact to urge an article of clothing 8 placed on the plates 42 into a predetermined orientation. Similarly, one embodiment of apparatus 10 features the folding assembly 40 defining at least one channel 46 that is configured to facilitate passage of a portion of an article of clothing 8 through the passage 14 when urged into a predetermined orientation.

For example, in one embodiment, folding assembly 40 comprises a collection of different geometries, i.e., plates 42, manipulation members 44, channels 46, that are configured to interact to fold the sleeves of a business shirt behind the body to facilitate ironing thereof as the shirt passes through the passage 14. Variations hereon are possible and within the scope of the present disclosure.

The skilled addressee is to appreciate that actuation of the folding assembly 40 may be performed by hand, by means of a suitable actuator, as is known in the art, or the like. Such actuation may occur on a dynamic basis as needed, such as an actuator extending or moving plate(s) 42 and/or manipulation member(s) 44 when the article of clothing 8 reaches a particular position along the passage 14, or may be done passively, where the plate(s) 42 and/or manipulation member(s) 44 are placed in a static position, etc. Alternatively, or additionally, actuation of the folding assembly 40 may be performed by hand prior to use of the apparatus 10, upon initial activation of the apparatus 10, or the like.

In one embodiment, the sensor 30 is configured to sense specific characteristics of the article of clothing 8, such as fabric type, fabric composition, fabric density, type of item of clothing, e.g., shirts, trousers, etc., or the like. Such sensed characteristics can be used to determine operation of the folding assembly 40 and/or a specific treatment regime, as described in more detail below.

As will be further appreciated by the skilled addressee, the guiding arrangement 16 may take any number of forms, requirements depending. For example, in one embodiment, the guiding arrangement 16 may include at least one roller that is configured to feed the article of clothing 8 through the passage 14. Such at least one roller may be offset or angled relative to the passage 14 in order to stretch or similarly urge or impart a biasing force to the article of clothing. In other embodiments, or additionally, the guiding arrangement 16 may include an endless belt conveyor feeder configured to feed the article of clothing through the passage.

In a yet further embodiment, the guiding arrangement 16 may include a hanger urger mechanism configured to engage a suitable hanger in receipt of such article 8 of clothing and to urge the hanger through the passage 14. For example, the hanger urger mechanism may comprise a hook or fitting to which a clothes hanger containing the article of clothing 8 can be fastened, e.g., in a magnetic and/or non-magnetic manner, with a suitable actuator drawing or pulling the hanger with article of clothing 8 through the passage 14. Such a mechanism may be realized in a number of ways as known in the art and will not be described in any detail herein. The skilled addressee is to appreciate that the hanger may comprise any suitable device for locating or positioning the article of clothing as required, such as a specific template or similar device.

In an embodiment, the at least one treatment assembly comprises a pre-treatment assembly 18 within the housing 12 and configured to pre-treat the article of clothing 8 as the article is guided through the passage 14. Alternatively, or additionally, the at least one treatment assembly may also comprise a primary treatment assembly 20 within the housing 12 and configured to treat the article of clothing 8 as the article is guided through the passage 14, and/or the at least one treatment assembly may comprise a post-treatment assembly 22 configured to post-treat the article of clothing 8 as the article is guided through the passage 14. Variations hereon are possible and within the scope of the present disclosure.

In the embodiment exemplified in the figures, apparatus 10 includes a pre-treatment assembly 18 within the housing 12, which is configured to pre-treat the article of clothing 8 as the article is guided or fed through the passage 14. For example, in one embodiment, the pre-treatment assembly includes a fluid applicator configured to pre-treat the article of clothing 8 by applying or spraying an ironing fluid 32 thereto. In such an embodiment, the fluid applicator typically includes atomizer nozzles for spraying the ironing fluid onto the article of clothing 8, along with necessary pumps, conduits and the like to realize this.

The ironing fluid 32 may comprise any desired fluid, such as a gas or a liquid, for providing a desired effect. In one example, the ironing fluid may comprise regular water, but other embodiments may include chemical compositions, starch solutions, fragrances, etc. Typically, apparatus 10 includes at least one reservoir (as shown) for storing such ironing fluid, along with suitable pumps and the like to discharge the fluid as required.

Apparatus 10 also includes primary treatment assembly 20 within the housing 12, which is configured to treat the article of clothing 8 as the article is guided through the passage 14. In a typical embodiment, the primary treatment assembly 20 comprises at least one plate and/or roller configured to iron the article of clothing 8 by applying heat and/or pressure thereto. Accordingly, such primary treatment plate(s) and/or roller(s) are typically heated, e.g., resistive heating, induction heating, etc., to facilitate primary treatment ironing, as is known in the art. Similarly, suitable actuators may be implemented to apply pressure via such plate(s) and/or roller(s).

In one embodiment, the primary treatment plate(s) and/or roller(s) comprises fluid channels and/or nozzles for delivering ironing fluid to the plate(s) and/or roller(s) during primary treatment of the article of clothing 8. For example, such fluid channels or nozzles may deliver water that is subsequently converted to steam on a hot surface of the plate(s) and/or roller(s) during primary treatment.

In another embodiment, the primary treatment assembly 20 may include a steam chamber through which the article of clothing 8 is passed in order to facilitate primary treatment ironing. Variations hereon are possible and within the scope of the present disclosure.

Generally, following the primary treatment assembly 20, apparatus 10 includes post-treatment assembly 22, which is configured to post-treat the article of clothing 8 as the article is guided through the passage 14. The skilled addressee is to appreciate that the post-treatment assembly 22 may include a number of different configurations, requirements depending. For example, post-treatment assembly 22 may comprise a fluid applicator configured to post-treat the article of clothing 8 by applying a post-treatment fluid thereto. Such post-treatment fluid may include steam via a suitable steam applicator for applying high temperature steam to the article of clothing for hygienic purposes. Such a fluid applicator may also include a scent or fragrance applicator configured to apply a particular scent or fragrance to the article of clothing.

In another embodiment, or additionally, the post-treatment assembly 22 may comprise an infra-red (IR) emitter configured to post-treat the article of clothing 8 by applying infra-red or near infra-red radiation thereto in order to facilitate evaporation of ironing fluid from the article of clothing 8. Similarly, in another embodiment, or additionally, the post-treatment assembly 22 may comprise an ultra-violet emitter configured to post-treat the article of clothing by applying ultra-violet radiation thereto in order to facilitate elimination of bacteria therefrom.

In a yet further embodiment, or additionally, the post-treatment assembly 22 may comprise an ultrasonic emitter configured to post-treat the article of clothing by applying ultrasonic radiation thereto in order to facilitate evaporation of ironing fluid therefrom. In another embodiment, or again additionally, the post-treatment assembly 22 may comprise an electrostatic discharge emitter configured to post-treat the article of clothing by applying electrostatic discharge thereto in order to facilitate loosening of intermolecular bonds of the fabric of the article of clothing.

In another embodiment, or additionally, the post-treatment assembly 22 may comprise a thermoelectric heat recovery mechanism configured to recover heat energy from the article of clothing, e.g., excess heat following primary treatment. In an embodiment, such recovered heat energy is provided to the electrostatic discharge emitter, but variations hereon are possible and within the scope of the present disclosure.

In another embodiment, or additionally, the post-treatment assembly 22 may comprise at least one pressure roller 34 configured to post-treat the article of clothing by applying a predetermined amount of pressure thereto in order to facilitate wrinkle removal. In an embodiment, the at least one pressure roller 34 may comprise an outer layer of material, such as thermal foam, sponge or fabric to impede mechanical damage to fasteners of the article of clothing, e.g., buttons, clasp locker, etc.

While general embodiments of the treatment assemblies 18, 20, and 22 have been provided, the skilled addressee is to appreciate that an order of the treatment assemblies may differ or vary between different embodiments. For example, one embodiment may start an ironing process with a primary treatment as described above, followed by a pre-treatment and post-treatment. Accordingly, a specific function and/or order of the described treatment assemblies 18, 20, 22 is interchangeable, requirements depending. For example, ironing fluid application may be performed by the primary treatment assembly 20, with heat and pressure application performed by the pre- or post-treatment assemblies 18 or 22, respectively.

Apparatus 10 further generally includes controller 24, which is configured to control the guiding arrangement 16 and treatment assemblies 18, 20, and 22. In a typical embodiment, the controller 24 is configured to control the guiding arrangement 16 and treatment assemblies 18, 20, and 22 according to a sensed characteristic of the article of clothing, as sensed via sensor 30. Accordingly, the controller 24 is generally programmed with a specific treatment regime for an article of clothing, the treatment regime determined by the sensed characteristics.

For example, different treatment regimes may be applied to different types of fabric, as is generally known in the art. A cotton dress shirt may require different pre-treatment, primary treatment and post-treatment as compared to a woolen blouse. Such treatment regimes will not be described in detail herein, but typically involve a determination of application of ironing fluid (as well as an amount of fluid to apply), specific temperature to apply, specific pressure to apply, specific post-treatment to apply, duration of treatments applied, a speed or rate at which the guiding arrangement 16 feeds the article of clothing through the passage, and/or the like.

In another embodiment, the controller 24 is programmed with a specific treatment regime for an article of clothing, the treatment regime manually selectable by a user. Accordingly, in such an embodiment, the controller 24 typically includes a suitable user interface (not shown) to allow treatment regime selection. For example, apparatus 10 may include a network interface with a smartphone providing a GUI, via a suitable application or "app," via which a treatment regime is selectable, or a dial, button input, touchscreen, and/or the like. Variations hereon are possible and within the scope of the present disclosure.

Finally, apparatus 10 generally includes some manner of energizing means 36, which is configured to provide electrical energy to the controller 24, guiding arrangement 16 and treatment assemblies 18, 20, and 22. Typically, the energizing means 36 comprises an electrical power supply, as is known in the art, that operatively draws electrical power from a mains power connection and/or suitable electrochemical cells, such as batteries. In an embodiment, the apparatus 10 may include rechargeable batteries to allow remote operation, such as when travelling.

The skilled addressee is also to appreciate that the present disclosure extends to an associated method of automatic ironing. Such a method generally comprises the steps of providing automatic ironing apparatus 10, as described herein, and inserting an article of clothing into the passage 14 of the apparatus 10 so that the apparatus 10 automatically irons the article of clothing. As described above, the method may include the step of a user selecting a suitable treatment regime for the apparatus 10 to treat the article of clothing.

It is believed to be particularly advantageous that the present disclosure provides for apparatus 10 to be able to automatically iron an article of clothing. It is further believed to be of benefit that apparatus 10 can sense a suitable treatment regime for ironing the article of clothing 8, and that apparatus 10 envisages a variety of treatment options to allow efficient and proper automatic ironing.

Optional embodiments of the present disclosure may also be said to broadly include the parts, elements and features referred to or indicated herein, individually or collectively, in any or all combinations of two or more of the parts, elements or features, and wherein specific integers are mentioned herein that have known equivalents in the art to which the disclosure relates, such known equivalents are deemed to be incorporated herein as if individually set forth. In the example embodiments, well-known processes, well-known device structures, and well-known technologies are not described in detail, as such will be readily understood by the skilled addressee.

The use of the terms “a,” “an,” “the,” and/or similar referents in the context of describing various embodiments (especially in the context of the claimed subject matter) are to be construed to cover both the singular and the plural, unless otherwise indicated herein or clearly contradicted by context. The terms “comprising,” “having,” “including,” and “containing” are to be construed as open-ended terms (i.e., meaning “including, but not limited to,”) unless otherwise noted. As used herein, the term “and/or” includes any and all combinations of one or more of the associated listed items. No language in the specification should be construed as indicating any non-claimed subject matter as essential to the practice of the claimed subject matter.

Spatially relative terms, such as “inner,” “outer,” “beneath,” “below,” “lower,” “above,” “upper,” and the like, may be used herein for ease of description to describe one element or feature’s relationship to another element(s) or feature(s) as illustrated in the figures. Spatially relative terms may be intended to encompass different orientations of the device in use or operation in addition to the orientation depicted in the figures. For example, if the device in the figures is turned over, elements described as “below” or “beneath” other elements or features would then be oriented “above” the other elements or features. Thus, the example term “below” can encompass both an orientation of above and below. The device may be otherwise oriented (rotated 90 degrees or at other orientations) and the spatially relative descriptors used herein interpreted accordingly.

It is to be appreciated that reference to “one example” or “an example” of the disclosure, or similar exemplary language (e.g., “such as”) herein, is not made in an exclusive sense. Various substantially and specifically practical and useful exemplary embodiments of the claimed subject matter are described herein, textually and/or graphically, for carrying out the claimed subject matter.

Accordingly, one example may exemplify certain aspects of the disclosure, while other aspects are exemplified in a different example. These examples are intended to assist the skilled person in performing the disclosure and are not intended to limit the overall scope of the disclosure in any way unless the context clearly indicates otherwise. Variations (e.g., modifications and/or enhancements) of one or more embodiments described herein might become apparent to those of ordinary skill in the art upon reading this disclosure. It is expected that skilled artisans will employ such variations as appropriate, and that the claimed subject matter will be practiced other than as specifically described herein.

The invention claimed is:

1. An automatic ironing apparatus comprising:

a man-portable housing defining an inlet on a first side and an outlet on a second side thereof that is opposite the first side, the inlet and the outlet arranged in register via a passage;

a guiding arrangement configured to guide an article of clothing through the passage, the guiding arrangement including a folding assembly configured to urge the article of clothing into a predetermined orientation to facilitate treatment thereof as the article of clothing is guided through the housing;

treatment assemblies comprising:

a pre-treatment assembly within the housing and configured to pre-treat the article of clothing as the article of clothing is guided through the passage;

a primary treatment assembly within the housing and configured to treat the article of clothing as the article of clothing is guided through the passage; and a post-treatment assembly configured to post-treat the article of clothing as the article of clothing is guided through the passage;

a controller configured to control the guiding arrangement and the treatment assemblies; and energizing means configured to provide electrical energy to the controller, the guiding arrangement, and the treatment assemblies, wherein each of the treatment assemblies facilitates ironing of the article of clothing as the article of clothing is automatically guided through the passage.

2. The automatic ironing apparatus of claim 1, wherein the folding assembly comprises at least two articulated plates slidably arranged within the housing, the at least two articulated plates configured to interact to urge the article of clothing placed thereon into the predetermined orientation.

3. The automatic ironing apparatus of claim 2, wherein the folding assembly includes at least one manipulation member configured to interact with the at least two articulated plates in order to interact to urge the article of clothing placed thereon into the predetermined orientation.

4. The automatic ironing apparatus of claim 2, wherein the folding assembly defines at least one channel disposed within the at least two articulated plates, at least a portion of the at least one channel extending underneath a portion of the at least two articulated plates, the at least one channel configured to facilitate passage of a portion of the article of clothing through the passage when urged into the predetermined orientation.

5. The automatic ironing apparatus of claim 4, wherein the folding assembly includes at least one manipulation member configured to interact with the at least two articulated plates in order to interact to urge the article of clothing placed thereon into the predetermined orientation, the at least one manipulation member being aligned with a lower surface and a side surface of the at least one channel.

6. The automatic ironing apparatus of claim 1, wherein the guiding arrangement includes at least one sensor configured to sense one or more of a presence and a characteristic of the article of clothing at the inlet of the housing, the one or more of the sensed presence and the sensed characteristic communicated to the controller to control the guiding arrangement.

7. The automatic ironing apparatus of claim 6, wherein the at least one sensor is configured to sense the characteristic of the article of clothing, the characteristic of the article of clothing selected from a group consisting of fabric type, fabric composition, fabric density, type of clothing article, and shape of the article of clothing.

8. The automatic ironing apparatus of claim 7, wherein the controller is programmed with a specific treatment regime for the article of clothing, the controller configured to control one or more of the guiding arrangement and the treatment assemblies according to a sensed characteristic of the article of clothing.

9. The automatic ironing apparatus of claim 1, wherein the pre-treatment assembly includes a fluid applicator configured to pre-treat the article of clothing by applying an ironing fluid thereto.

10. The automatic ironing apparatus of claim 1, wherein the post-treatment assembly comprises a fluid applicator configured to post-treat the article of clothing by applying a post-treatment fluid thereto.

11. A method of automatic ironing, comprising:

providing the automatic ironing apparatus of claim 1; and inserting the article of clothing into the passage of the automatic ironing apparatus so that the automatic ironing apparatus automatically irons the article of clothing.

12. The method of claim 11, further comprising a user selecting a treatment regime for the automatic ironing apparatus to treat the article of clothing.

* * * * *